United States Patent

Klimkowski et al.

(10) Patent No.: US 6,660,739 B1
(45) Date of Patent: Dec. 9, 2003

(54) HETEROCYCLIC AMIDES AS INHIBITORS OF FACTOR XA

(75) Inventors: Valentine Joseph Klimkowski, Carmel, IN (US); Jeffrey Alan Kyle, Fishers, IN (US); John Joseph Masters, Fishers, IN (US); Michael Robert Wiley, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/857,748

(22) PCT Filed: Dec. 15, 1999

(86) PCT No.: PCT/US99/29834

§ 371 (c)(1),
(2), (4) Date: Jun. 8, 2001

(87) PCT Pub. No.: WO00/39092

PCT Pub. Date: Jul. 6, 2000

Related U.S. Application Data

(60) Provisional application No. 60/113,595, filed on Dec. 24, 1998.

(51) Int. Cl.[7] .................... A61K 31/496; C07D 401/06; C07D 405/14; C07D 409/14
(52) U.S. Cl. ............... 514/252.11; 514/253.11; 514/253.13; 544/357; 544/364; 544/365
(58) Field of Search ................ 544/357, 364; 544/365; 514/252.11, 253.13, 253.11

(56) References Cited

U.S. PATENT DOCUMENTS 6,225,309 B1 * 5/2001 Faull et al. ................ 514/218

FOREIGN PATENT DOCUMENTS

| EP | 097 630 | 1/1984 |
|----|---------|--------|
| EP | 1 031 563 | 8/2000 |
| WO | WO 96/10022 | 4/1996 |
| WO | WO 98/54164 | 12/1998 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | WO 99/16747 | 8/1999 |
| WO | WO 00/39111 | 7/2000 |
| WO | WO 00/39117 | 7/2000 |
| WO | WO 00/39118 | 7/2000 |

OTHER PUBLICATIONS

Zhu et al. in "Annual Reports in Medicinal Chemistry", vol.35, pp.83–102 (2000).*

Vacca, Joseph P. (Annette M. Doherty Section Editor), Annual Reports in Medicinal Chemistry, (1998), 33, 81–90.

* cited by examiner

Primary Examiner—Emily Bernhardt
(74) Attorney, Agent, or Firm—Thomas E. Jackson

(57) ABSTRACT

This application relates to a compound of formula I

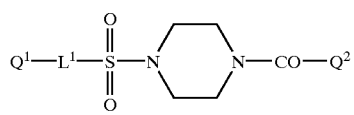

(or a pharmaceutically acceptable salt thereof) as defined herein, pharmaceutical compositions thereof, and its use as an inhibitor of factor Xa, as well as a process for its preparation and intermediates therefor.

10 Claims, No Drawings

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Chromogenic Substrate for Factor Xa
<221> NAME/KEY: MOD_RES
<222> LOCATION: (1)..(1)
<223> OTHER INFORMATION: ACETYLATION
<221> NAME/KEY: MOD_RES
<222> LOCATION: (4)..(4)
<223> OTHER INFORMATION: AMIDATION

<400> SEQUENCE: 1

Ile Glu Gly Arg
1

HETEROCYCLIC AMIDES AS INHIBITORS OF FACTOR XA

This application is a 371 of PCT/US99/29834 filed Dec. 15, 1999 which claims the benefit of U.S. Provisional Application No. 60/113,595, filed Dec. 24, 1998.

This invention relates to antithrombotic heterocyclic amides which demonstrate activity as inhibitors of factor Xa and, accordingly, which are useful anticoagulants in mammals. In particular it relates to heterocyclic amides having high anticoagulant activity, and antithrombotic activity. Thus, this invention relates to new amides which are inhibitors of factor Xa, pharmaceutical compositions containing the amides as active ingredients, and the use of the amides as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of 4 thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Joseph P. Vacca (Annette M. Doherty Section Editor), *Annual Reports in Medicinal Chemistry*, (1998), 33, 81–90, as well as WO 96/10022.

Although the heparins and coumarins are effective anticoagulants, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the amides of the present invention, as defined below, are potent inhibitors of factor Xa which may have high bioavailability following oral administration.

According to the invention there is provided a compound of formula I

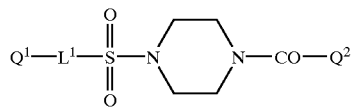

(or a pharmaceutically acceptable salt thereof) wherein:
$Q^1$ is phenyl or 2-naphthalenyl either of which may bear one or more halo, trifluoromethyl, methoxy or methyl substituents;
$L^1$ is a direct bond, methylene, ethylene or ethen-1,2-diyl; and
$Q^2$ is $Q^{2A}$, $Q^{2B}$, or $Q^{2C}$ in which
$Q^{2A}$ (showing the CO to which it is attached) is

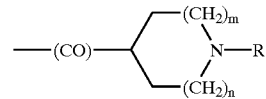

in which each of m and n independently is 0 or 1;
$Q^{2B}$ is 1-piperazinyl which bears at the 4-position the group R; and
$Q^{2C}$ is 3,4-didehydropiperidin-4-yl which bears at the 1-position the group R; and
R is t-butyl, —$CHR^yR^z$, or —$CHR^wR^x$ wherein each of $R^w$ and $R^x$ independently is hydrogen or (1–3C)normal alkyl-, or —$CHR^wR^x$ is 2-indanyl or (showing the nitrogen to which it is attached) is

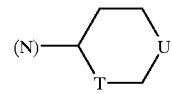

in which T is a single bond or methylene and U is methylene, ethylene, oxy, —$S(O)_q$— (wherein q is 0, 1 or 2) or imino (which may bear a methyl substituent), or T is ethan-1,1-diyl and U is a single bond or methylene;
$R^y$ is hydrogen or methyl; and
$R^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen).

As used herein, the expression a compound of formula I or the expression a compound of the invention includes the compound and any conventional prodrug thereof, as well as a pharmaceutically acceptable salt of said compound or prodrug.

A particular compound of formula I is one wherein
$Q^1$ is phenyl or 2-naphthalenyl either of which may bear a chloro substituent;
$L^1$ is a direct bond or trans-ethen-1,2-diyl; and $Q^{2A}$ is $Q^{2A}$, $Q^{2B}$, or $Q^{2C}$ in which
  $Q^{2A}$ is 4-piperidinyl which bears at the 1-position the group R;
  $Q^{2B}$ is 1-piperazinyl which bears at the 4-position the group R; and
  $Q^{2C}$ is 3,4-didehydropiperidin-4-yl which bears at the 1-position the group R;
    R is —$CHR^yR^z$ or —$CHR^wR^x$ wherein
      each of $R^w$ and $R^x$ independently is hydrogen or. (1–3C)normal alkyl; or —$CHR^wR^x$ is 2-indanyl or (showing the nitrogen to which it is attached) is

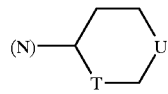

in which T is a single bond or methylene and U is methylene, ethylene, oxy, —$S(O)_q$— (wherein q is 0, 1 or 2) or imino (which may bear a methyl substituent), or T is ethan-1,1-diyl and U is a single bond or methylene;
  $R^y$ is hydrogen or methyl; and
  $R^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen).

A pharmaceutically acceptable salt of an antithrombotic agent of the instant invention includes one which is an acid-addition salt made from a basic compound of formula I and an acid which provides a pharmaceutically acceptable anion. Thus, a salt of a novel compound of formula I as provided herein made with an acid which affords a pharmaceutically acceptable counter ion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–3C)normal alkyl is methyl, ethyl or propyl; and for (3–6C)cycloalkyl is cyclopropyl, cyclobutyl, cyclopentyl or cyclohexyl. A particular value for halo is bromo or chloro, and more particularly is chloro.

A particular value for $Q^1$ is 4-chlorophenyl or 6-chloronaphthalen-2-yl. A particular value for —$L^1$—$Q^1$ is 4-chloro-trans-styryl or 6-chloronaphthalen-2-yl. A particular value for $Q^2$ is 1-isopropylpiperidin-4-yl, 1-cyclohexylpiperidin-4-yl, 4-isopropylpiperazin-1-yl, or 1-(tetrahydropyran-4-yl)piperidin-4-yl.

Particular species include those listed below in the examples.

It will be appreciated that certain compounds of formula I (or salts or prodrugs, etc.) may exist in, and he isolated in, isomeric forms, including tautomeric forms, cis- or trans-isomers, as well as optically active, racemic, or diastereomeric forms. It is to be understood that the present invention encompasses a compound of formula I in any, of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

A compound of formula I may be prepared by processes which include processes known in the chemical art for the production of structurally analogous compounds or by a novel process described herein. A process for the preparation of a compound of formula I (or a pharmaceutically acceptable salt thereof) and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I (or a pharmaceutically acceptable salt thereof) as provided in any of the above descriptions which is selected from any of those described in the examples, including the following.

(A) Acylating an amine of formula II,

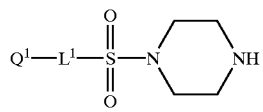

II using a corresponding acid of formula HO—CO—$Q^2$, or an activated derivative thereof. Typical activated derivatives include the acid halides, activated esters, including 4-nitrophenyl esters and those derived from coupling reagents. Typical procedures include one similar to that described at example 1-E for the preparation of a protected intermediate.

(B) for a compound of formula I in which $Q^2$ is $Q^{2B}$, acylating a piperazine of formula H—$Q^{2B}$ using an activated derivative of an acid of formula III,

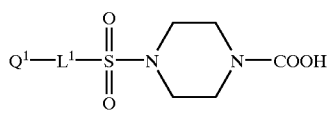

III particularly the corresponding acid chloride or 4-nitrophenyl ester.

(C) For a compound of formula I in which R is —$CHR^yR^z$ or —$CHR^wR^x$, alkylating the amino nitrogen of a corresponding compound of formula I in which R is hydrogen using an alkylating agent of formula Y—$CHR^yR^z$ or Y—$CHR^wR^x$ or, preferably, reductively alkylating the amine using a compound of formula $R^y$—CO—$R^z$ or $R^w$—CO—$R^x$. The direct alkylation may be completed in a polar solvent in the presence of a base. The reductive alkylation conveniently is carried out, for example as described in the examples, using sodium cyanoborohydride in methanol/acetic acid or using sodium triacetoxyborohydride in an inert solvent such as 1,2-dichloroethane along with glacial acetic acid and an excess of the carbonyl compound.

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

A novel intermediate or starting material compound provides a further aspect of the invention. The various starting material may be made by processes which include processes known in the chemical art for the production of structurally analogous compounds or by a novel process described herein or one analogous thereto.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which there is a hydroxy, but in which the corresponding substituent is —$OP^P$ in place of hydroxy, wherein PP is a phenol protecting group other than methyl. Phenol protecting groups are well known in the art, for example as described in T. W. Greene and P. G. M. Wuts, "Protecting Groups in Organic Synthesis" (1991). Further, $P^p$ may denote a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, enylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to. permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoaculability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA), and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anticoagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 4.5 mesh U.S. sieve, and filled into hard gelatin capsules in 200 mg quantities.

Formulation 6: Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| | |
|---|---|
| Active ingredient | 50 mg |
| Sodium in carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The ability of a compound of the present invention to be an effective and orally active factor Xa inhibitor may be evaluated in one or more of the following assays or in other standard assays known to those in the art.

The inhibition by a compound of the Inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

$$\text{Enzyme} + I \rightleftharpoons \text{Enzyme-I}$$

$$K_{ass} = \frac{[\text{Enzyme-I}]}{[(\text{Enzyme}) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 μL buffer (0.03 M Tris, 0.15 M NaCl pH 7) in each well, followed by 25 μL of inhibitor solution (in 100% methanol, or in 50% v:v aqueous methanol) and 25 μL enzyme solution; within two minutes, 150 μL aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA (SEQ ID NO: 1); 5.9 nM human thrombin -or 1.4 nM bovine trypsin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.81 mM HD-Ile-Pro-Arg-pNA; and 0.37 nM urokinase is used with 0.30 mM pyro-gfsGlu-Gly-Arg-pNA.

Kass is calculated for a range of concentrations of test compounds and the mean value reported in units of liter per mole. In general, a factor Xa inhibiting compound of formula I of the instant invention, as exemplified herein, exhibits a Kass of 0.1 to 0.5×106 L/mole or much greater.

The factor Xa inhibitor preferably should spare fibrinolysis induced by urokinase, tissue Dlasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction L-2 according to previous procedures and specification. Smith, *Bio-* chem. J., 185, 1–11 (1980; and Smith, et al., *Biochemistry*, 11, 2958–2967, (1972). Human fibrinogen (98 percent pure/ plasmin free) is from American Diagnostica, Greenwich, Connecticut. Radiolabeling of fibrinogen I-2 preparations is performed as previously reported. Smith, et al., *Biochemistry*, 11, 2958–2967, (1972) Urokinase is purchased from Leo Pharmaceuticals, Denmark, as 2200 Ploug units/vial. Streptokinas is purchased from Hoechst-Roussel Pharmaceuticals, Somerville, N.J.

Methods—Effects on Lysis of Human Plasma Clots by t-PA

Human plasma clots are formed in micro test tubes by adding 50 $\mu$L thrombin (73 NIH unit/mL) to 100 $\mu$L human plasma which contains 0.0229 $\mu$Ci 125-iodine labeled fibrinogen. Clot lysis is studied by overlaying the clots with 50 $\mu$L of urokinase or streptokinase (50, 100, or 1000 unit/mL) and incubating for 20 hours at room temperature. After incubation the tubes are centrifuged in a Beckman Microfuge. 25 $\mu$L of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 $\mu$g/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988) A CoAScreener coagulation instrument (American LABor, Inc.) is used for all coagulation assay measurements. The prothrombin time (PT) is measured by adding. 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.).and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous. administration and at 1, 2, 4, and 6 hour after oral. dosing. Plasma is analyzed for drug concentration using an HPLC procedure involving C8 Bond Elute (Varion) cartridges for sample preparation and a methanol/30 nM ammonium acetate buffer (pH 4) gradient optimized for each compound. % Oral bioavailability is calculated by the following equation:

$$\% \text{ Oral Bioavailability} = \frac{\text{AUC po}}{\text{AUC iv}} \times \frac{\text{Dose iv}}{\text{Dose po}} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y., 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model.

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolys s is defined as zero CBF which persisted for at least 30 minutes.

Hematology and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl

Anal.=elemental analysis aq=aqueous

Boc=t-butyloxycarbonyl

Calcd=calculated

DMF=dimethylformamide
DMSO=dimethylsulfoxide
FTIR=Fourier transform IR
HPLC=High Performance Liquid Chromatography
IR=Infrared Spectrum
MS-FD or MS (FD)=field desorption mass spectrum
MS-IS (or IS-MS)=ion spray mass spectrum
NMR=Nuclear Magnetic Resonance
RPHPLC=Reversed Phase High Performance Liquid Chromatography
RT (or $R_t$)=retention time
satd=saturated
SCX=strong cation exchange (resin)
TFA=trifluoroacetic acid
THF=tetrahydrofuran Unless otherwise stated, pH adjustments and work up are with aqueous acid or base solutions. $^1$H-NMR indicates a satisfactory NMR spectrum was obtained for the compound described. IR (or FTIR) indicates a satisfactory infra red spectrum was obtained for the compound described.

Analytical HPLC method was a linear gradient of 90/10 to 50/50 (0.1% TFA in water/0.1% TFA in acetonitrile) over 40 minutes with a flow rate of 1 mL/min.

EXAMPLES 1–13

Examples 1–13 are of the following general formula in which the value of R is defined for each example.

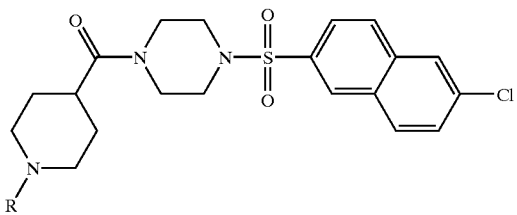

EXAMPLES 1

Preparation of 1-(Piperidin-4-yl-carbonyl)-4-(6-chloro-naphthalen-2-ylsulfonyl)piperazine Trifluoroacetate (R=H)

A. 6-Chloro-2-naphthalenesulfonic Acid

6-Amino-2-napthalenesulfonic acid (88.0 g, 0.4 mol) was suspended in 5 N HCl (200 mL) and water (150 mL) and cooled to 3° C. A solution of sodium nitrite (27.0 g, 0.4 mol) in water (50 mL) was added dropwise over two hours. After one additional hour, the mixture was poured in several portions into a stirred suspension of copper(I) chloride (39.6 g, 60.6 mmol) in 5 N HCl (200 mL). Considerable foaming occurred during this addition. After standing overnight at room temperature, the mixture was concentrated on a rotary evaporator to a brown solid that was then dried in a vacuum oven overnight at 100° C. to provide the acid (111.9 g)

B. 6-Chloro-2-naphthalenesulfonyl Chloride

To a stirring solution of naphthalene sulfonic acid (12 g) in DMF (40 mL) at 0° C. was added dropwise thionyl chloride (9 mL). After 3 h the mixture was poured over ice then extracted twice with methylene chloride. The combined organic extracts were washed with water and brine, and dried over sodium sulfate, then adsorbed onto silica and filtered through a pad of silica, eluting with 50% ethyl acetate: 50% hexanes. The solvents were then evaporated in vacuo to give 2.8 g of oil that crystallized on standing. The product was chromatographed on a (Biotage) silica column, eluting with ethyl acetate:hexanes (1:9), to yield 1.6 g pure product.

$^1$H-NMR (CDCl$_3$): δ (dd, 1H, 7.64, J=1,12), (m, 4H, 7.9–8.2), (s, 1H, 8,6); MS (FD) 259.9 M+.

C. 1-boc-4-(6-Chloronaphthalen-2-ylsulfonyl)piperazine

To a stirring solution of N-Boc-piperazine (400 mg, 2.1 mmol) and triethylamine (1 mL, 7 mmol) in methylene chloride (5 mL) was added 6-chloro-2-naphthalenesulfonyl chloride (500 mg, 1.9 mmol). After 2 h the solution was washed with water, dried over sodium sulfate and evaporated. The residue was chromatographed on a (Biotage) silica column eluting with ethyl acetate:hexanes (2:8) to give 300 mg (38%). $^1$H-NMR (CDCl$_3$): δ (s, 9H, 1.4), (m, 4H, 3.07), (m, 4H, 3.55), (dd, 1H, 7.55, J=1,12), (dd, 1H, 7.75, J=1,12), (m, 4H, 7.9), (s, 1H, 8.3), MS (FD) 410.1 M+; IR (chloroform) carbonyl 1691 cm$^{-1}$. Anal. Calcd: C, 55.54; H, 5.64; N, 6.82; Cl, 8.63; Found: C, 55.71; H, 5.76; N, 6.85; Cl, 8.76.

D. 1-(6-Chloronaphthalen-2-ylsulfonyl)piperazine

To a stirring suspension of 1-Boc-4-(6-chloro-naphthalen-2-ylsulfonyl)piperazine (2.8g, 6.8 mmol) in dioxane (50 mL) was added 4 M HCl in dioxane (5 mL, 40 mmol). After stirring overnight at room temperature, the solvent was evaporated in vacuo, and the residue was dissolved in water. The aqueous phase was and made basic with 5 N NaOH and extracted twice with ethyl acetate. The combined extracts were washed with water and brine, then dried over sodium sulfate and evaporated to 2.1 g (100%) solid.

$^1$H-NMR (DMSO-d$^6$): δ (m, 4H, 2.71), (m, 4H, 2.86), (dd, 1H, 7.7, J=1, 10), (dd, 1H, 7.8, J=1, 10), (d, 1H, 8.16, J=10), (s, 1H, 8.22), (d, 1H, 8.25, J=10), (s, 1H, 8.48); MS 311.2 (M+1). Anal. Calcd: C, 54.10; H, 4.86; N, 9.01; Cl, 11.41; Found: C, 54.20; H, 4.88; N, 8.85; Cl, 11.66.

E. 1-(1-boc-Piperidin-4-ylcarbonyl)-4-(6-chloronaphthalen-2-ylsulfonyl)piperazine To a stirring solution of N-Boc-isonipecotic acid (1.99 g, 8.7 mmol) in THF (50 mL) was added sodium ethoxide (0.592 g, 8.7 mmol) After 0.5 h, the solvent was removed in vacuo and the residue was suspended in dichloromethane (50 mL). To this mixture was added a couple drops of DMF, followed by oxalyl chloride (1.32 g, 10.4 mmol). After stirring for another hour, the solvent was removed in vacuo and the crude acid chloride resuspended in dichloromethane (25 mL). To this solution was added a solution of 1-(6-chloronaphthalen-2-ylsulfonyl)piperazine (1.8 g, 5.8 mmol) and pyridine (5 mL) in dichloromethane (25 mL) After stirring overnight, the solvent was removed in vacuo and the residue was partitioned between ethyl acetate and water. The layers were separated and the organic phase was washed twice with 1 M citric acid, once with brine, twice with satd aq NaHCO$_3$ and twice again with brine, then dried with MgSO$_4$, filtered and concentrated in vacuo. The residue was then dissolved in a minimum amount of dichloromethane and chromatographed over silica gel, eluting with a step gradient of 35% ethyl acetate in hexanes through 75% ethyl acetate in hexanes. The product containing fractions were combined and concentrated in vacuo to give 2.1 g (69%) of a white foam.

$^1$H-NMR; IS-MS m/z 522.2 (MH+); Anal. for C$_{25}$H$_{32}$ClN$_3$O$_5$S: Calcd: C, 57.52; H, 6.18; N, 8.05; Found: C, 57.65; H, 6.19; N, 7.76.

F. 1-(Piperidin-4-ylcarbonyl)-4-(6-chloronaphthalen-2-yl-sulfonyl)piperazine Trifluoroacetate To a stirring solution of 1-(1-Boc-piperidin-4-yl-carbonyl)-4-(6-chloronaphthalen-2-ylsulfonyl)piperazine (2.2 g, 4.2 mmol) in dichloromethane (25 mL) was added anisole (2 mL) followed by TFA (25 mL). After 90 min, the solvents were removed in vacuo and the residue was dissolved in a few mL of dichloromethane and diluted with diethyl ether (200 mL). After stirring for 2 h, the suspension was sonicated and filtered and then the solid was washed with diethyl ether and dried in vacuo to give 2.25 g (99%) of a white solid.

$^1$H-NMR; IS-MS m/z 422.2 (MH+); Anal. for $C_{20}H_{24}ClN_3O_3S$.1.1TFA: Calcd: C, 48.71; H, 4.62; N, 7.68; F, 11.45; Found: C, 48.32; H, 4.65; N, 7.56; F, 11.36.

For the Preparation of the Compounds in Examples 2–13 Below, One of the Following Procedures was Used.

Procedure A:

1-(Piperidin-4-ylcarbonyl)-4-(6-chloronaphthalen-2-ylsulfonyl)piperazine trifluoroacetate (50 mg, 0.93 mmol) was placed in a 10 mL round-bottom flask and dissolved in methanol (1 mL). Aldehyde (0.112 mmol) or ketone (1 mL) and glacial acetic acid (0.050 mL) were added to the solution. Sodium cyanoborohydride (30 mg, 0.5 mmol) was then added. The reaction was stirred at room temperature until completion. The crude reaction mixture was then applied to a solid phase extraction (SPE) cartridge (strong cation exchange (SCX), 12 cc, 2 gram of packing material from Varian Sample Preparation Products, Harbor City, Calif.) that was pre-washed once 95:5 methanol:AcOH (10 mL). The cartridge was then washed once with methanol (10 mL). Product was eluted with 1.0 M ammonia in methanol (10 mL). The resulting solution was concentrated in vacuo to afford the alkylated product. If further purification was necessary, the product was dissolved in dichloromethane (3 mL) and applied to a silica gel cartridge (12 cc, 2 g of packing material from Varian Sample Preparation Products, Harbor City, Calif.). The cartridge was pre-washed with dichloromethane (10 mL). Product was eluted with dichloromethane to 96:4 dichloromethane:methanol. The resulting solution was concentrated in vacuo to afford the alkylated product in 26–100% yield.

Procedure B:

1-(Piperidin-4-ylcarbonyl)-4-(6-chloronaphthalen-2-ylsulfonyl)piperazine trifluoroacetate(50 mg, 0.093 mmol) was placed in a 10 mL round-bottom flask and suspended in 1,2-dichloroethane (1 mL). Benzaldehyde (1 mL) or 4-heptanone (1 mL) and glacial acetic acid (0.050 mL) was added to the solution. Sodium triacetoxyborohydride (100 mg, 0.5 mmol) was then added. The reaction was stirred at room temperature for 24 h. The crude reaction mixture was then applied to a solid phase extraction (SPE) cartridge (strong cation exchange (SCX), 12 cc, 2 gram of packing material from Varian Sample Preparation Products, Harbor City, Calif.) that was pre-washed once 95:5 methanol:AcOH (10 mL). The cartridge was then washed once with methanol (10 mL). Product was eluted with 1.0 M ammonia in methanol (10 mL). The resulting solution was concentrated in vacuo to afford the alkylated product. The product was dissolved in dichloromethane (3 mL) and applied to a silica gel cartridge (12 cc, 2 gram of packing material from Varian Sample Preparation Products, Harbor City, Calif.). The cartridge was pre-washed with dichloromethane (10 mL). Product was eluted with dichloromethane to 96:4 dichloromethane:methanol. The resulting solution was concentrated in vacuo to afford the alkylated product in 15–69% yield.

EXAMPLE 2

R=cyclopentyl; Procedure A; 46 mg, 100% (95% pure); Analytical RPHPLC, RT=22.68 min; IS-MS m/z 490.1 (MH+).

EXAMPLE 3

R=cyclohexyl; Procedure A; 46 mg, 98% (96% pure); Analytical RPHPLC, RT=24.55 min; IS-MS m/z 504.1 (MH+).

EXAMPLE 4

R=benzyl; Procedure B; 33 mg, 69% (96% pure); Analytical RPHPLC, RT=25.83 min; IS-MS m/z 512.1 (MH+).

EXAMPLE 5

R=cycloheptyl; Procedure A; 46 mg, 96% (97% pure); Analytical RPHPLC, RT=26.72 min; IS-MS m/z 518.2 (MH+).

EXAMPLE 6

R=(2-pyridyl)methyl; Procedure A; 24 mg, 50% (88% pure); Analytical RPHPLC, RT=21.04 min; IS-MS m/z 513.2 (MH+).

EXAMPLE 7

R=(3-pyridyl)methyl; Procedure A; 14 mg, 29% (91% pure); Analytical RPHPLC, RT=18.44 min; IS-MS m/z 513.1 (MH+).

EXAMPLE 8

R=(4-pyridyl)methyl; Procedure A; 21 mg, 44% (79% pure); Analytical RPHPLC, RT=17.40 min; IS-MS m/z 513.1 (MH+).

EXAMPLE 9

R=4-tetrahydropyranyl; Procedure A; 49 mg, 104% (93% pure); Analytical RPHPLC, RT=20.14 min; IS-MS m/z 506.1 (MH+).

EXAMPLE 10

R=4-thianyl; Procedure A; 45 mg, 92% (96% pure); Analytical RPHPLC, RT=23.03 min; IS-MS m/z 522.1 (MH+).

EXAMPLE 11

R=isopropyl; Procedure A; 43 mg, 100% (97% pure); Analytical RPHPLC, RT=20.76 min; IS-MS m/z 464.1 (MH+).

EXAMPLE 12

R=3-pentyl; Procedure A; 12 mg, 26% (96% pure); Analytical RPHPLC, RT=23.70 min; IS-MS m/z 492.1 (MH+).

EXAMPLE 13

R=4-heptyl; Procedure B; 7 mg, 15% (99% pure); Analytical RPHPLC, RT=29.51 min; IS-MS m/z 520.1 (MH+).

What is claimed is:

1. A compound of formula I

(or a pharmaceutically acceptable salt thereof) wherein:
$Q^1$ is phenyl or 2-naphthalenyl either of which may bear one or more halo, trifluoromethyl, methoxy or methyl substituents;
$L^1$ is a direct bond, methylene, ethylene or ethen-1,2-diyl; and
$Q^2$ is $Q^{2A}$, $Q^{2B}$, or $Q^{2C}$ in which
$Q^{2A}$ (showing the CO to which it is attached) is

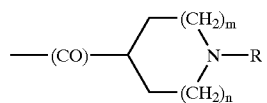

in which each of m and n independently is 0 or 1;
$Q^{2B}$ is 1-piperazinyl which bears at the 4-position the group R; and
$Q^{2C}$ is 3,4-didehydropiperidin-4-yl which bears at the 1-position the group R; and
R is t-butyl, —$CHR^yR^z$, or —$CHR^wR^x$ wherein
each of $R^w$ and $R^x$ independently is hydrogen or (1–3C)normal alkyl; or —$CHR^wR^x$ is 2-indanyl or (showing the nitrogen to which it is attached) is

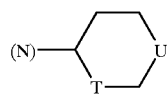

in which T is a single bond or methylene and U is methylene, ethylene, oxy, —$S(O)_q$— (wherein q is 0, 1 or 2) or imino (which may bear a methyl substituent), or T is ethan-1,1-diyl and U is a single bond or methylene;

$R^y$ is hydrogen or methyl; and
$R^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which has one to four heteroatoms selected from sulfur, oxygen and nitrogen or is a 6-membered aromatic ring which has one to three nitrogen atoms, wherein the heteroaryl is attached at carbon and may bear one or more methyl substituents on carbon or nitrogen); and
wherein halo is fluoro, chloro, bromo or iodo; (1–3C)normal alkyl is methyl, ethyl or propyl; and (3–6C)cycloalkyl is cyclopropyl, cyclobutyl, cyclopentyl or cyclohexyl.

2. A compound of claim 1 wherein
$Q^1$ is phenyl or 2-naphthalenyl either of which may bear a chloro substituent;
$L^1$ is a direct bond or trans-ethen-1,2-diyl; and
$Q^2$ is $Q^{2A}$, $Q^{2B}$, or $Q^{2C}$ in which
$Q^{2A}$ is 4-piperidinyl which bears at the 1-position the group R;
$Q^{2B}$ is 1-piperazinyl which bears at the 4-position the group R; and
$Q^{2C}$ is 3,4-didehydropiperidin-4-yl which bears at the 1-position the group R;
R is —$CHR^yR^z$ or —$CHR^wR^x$ wherein
each of $R^w$ and $R^x$ independently is hydrogen or (1–3C)normal alkyl; or —$CHR^wR^x$ is 2-indanyl or (showing the nitrogen to which it is attached) is

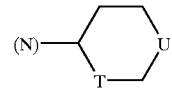

in which T is a single bond or methylene and U is methylene, ethylene, oxy, —$S(O)_q$— (wherein q is 0, 1 or 2) or imino (which may bear a methyl substituent), or T is ethan-1,1-diyl and U is a single bond or methylene;

$R^y$ is hydrogen or methyl; and $R^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which has one to four heteroatoms selected from sulfur, oxygen and nitrogen or is a 6-membered aromatic ring which has one to three nitrogen atoms, wherein the heteroaryl is attached at carbon and may bear one or more methyl substituents on carbon or nitrogen).

3. The compound of claim 2 wherein $Q^2$ is 1-isopropylpiperidin-4-yl, 1-cyclohexylpiperidin-4-yl, 4-isopropylpiperazin-1-yl, or 1-(tetrahydropyran-4-yl)-piperidin-4-yl.

4. The compound of claim 1 wherein $Q^2$ is 1-isopropylpiperidin-4-yl, 1-cyclohexylpiperidin-4-yl, 4-isopropylpiperazin-1-yl, or 1-(tetrahydropyran-4-yl)-piperidin-4-yl.

5. The compound of any of claims 1, 2, 4 and 3 wherein —$L^1$—$Q^1$ is 4-chloro-trans-styryl or 6 chloro-naphthalen-2-yl.

6. The pharmaceutically acceptable salt of a compound of formula I as claimed in claim 1 which is an acid-addition salt made from a basic compound of formula I and an acid which provides a pharmaceutically acceptable anion.

7. A pharmaceutical formulation comprising in association with a pharmaceutically acceptable carrier, diluent or excipient, a novel compound of formula I (or a pharmaceutically acceptable salt thereof) as provided in claim 1.

8. A process for preparing a compound of formula I (or a pharmaceutically acceptable salt thereof) as provided in claim 1 which is selected from (A) acylating an amine of formula II,

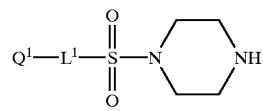

II using a corresponding acid of formula HO—CO—$Q^2$, or an activated derivative thereof;

(B) for a compound of formula I in which $Q^2$ is $Q^{2B}$, acylating a piperazine of formula H—$Q^{2B}$ using an activated derivative of an acid of formula III,

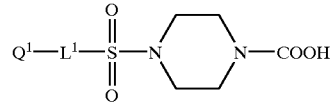

III (C) for a compound of formula I in which R is —$CHR^yR^z$ or —$CHR^wR^x$, alkylating the amino nitrogen of a corresponding compound of formula I in which R is hydrogen using an alkylating agent of formula Y—$CHR^yR^z$ or Y—$CHR^wR^x$ or reductively alkylating the amine using a compound of formula $R^y$—CO—$R^z$ or $R^w$—CO—$R^x$;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure;

and wherein, unless otherwise specified, $Q^1$, $L^1$ and $Q^2$ have any of the values defined in claim 1.

9. A method of inhibiting coagulation in a mammal comprising administering to a mammal in need of treatment, a coagulation inhibiting dose of a compound of formula I as provided in claim 1.

10. A method of treating a thromboembolic disorder comprising administering to a mammal in need of treatment, an effective dose of a compound of formula I as provided in claim 1.

* * * * *